United States Patent [19]

Darago

[11] Patent Number: 5,306,850
[45] Date of Patent: Apr. 26, 1994

[54] PURIFICATION PROCESS FOR A HYDROFLUOROALKANE

[75] Inventor: Gilles Darago, Tavaux, France

[73] Assignee: Solvay (Société Anonyme), Brussels, Belgium

[21] Appl. No.: 40,992

[22] Filed: Mar. 31, 1993

[30] Foreign Application Priority Data

Apr. 3, 1992 [FR] France ............... 92 04277

[51] Int. Cl.$^5$ ............... C07C 17/38; C07C 19/02
[52] U.S. Cl. ............... 570/178; 570/175
[58] Field of Search ............... 570/178

[56] References Cited

U.S. PATENT DOCUMENTS

| | | | |
|---|---|---|---|
| 2,831,902 | 4/1958 | Hamilton et al. | 570/178 |
| 3,689,373 | 9/1972 | Hutchinson | 570/178 |
| 4,548,701 | 10/1985 | Wolff | 570/178 |
| 4,766,261 | 8/1988 | Bierl | 570/178 |
| 4,968,850 | 11/1990 | Franklin et al. | 570/166 |
| 4,973,774 | 11/1990 | Rozen et al. | 570/178 |
| 5,001,287 | 3/1991 | Fernadez et al. | 570/178 |
| 5,120,461 | 6/1992 | Logsdon et al. | 570/121 |
| 5,122,294 | 6/1992 | Logsdon et al. | 570/121 |
| 5,200,431 | 4/1993 | Dattani et al. | 570/178 |

FOREIGN PATENT DOCUMENTS

| | | |
|---|---|---|
| 0361578 | 4/1990 | European Pat. Off. . |
| 0395793 | 11/1990 | European Pat. Off. . |
| 0395898 | 11/1990 | European Pat. Off. . |
| 0472391 | 2/1992 | European Pat. Off. . |
| 9118852 | 12/1992 | PCT Int'l Appl. . |
| 1625861 | 2/1991 | U.S.S.R. ............... 570/178 |
| 1031409 | 6/1966 | United Kingdom ............... 570/178 |

OTHER PUBLICATIONS

Chemical Abstracts, vol. 111, Dec. 25, 1989, No. 26, "35-Chemistry of Synthetic High Polymers", p. 145.

*Primary Examiner*—Joseph E. Evans
*Attorney, Agent, or Firm*—Spencer, Frank & Schneider

[57] ABSTRACT

Process for purifying a hydrofluoroalkane with respect to impurities which are less volatile than the hydrofluorocarbon, by distillation in the presence of an acid-scavenger, for example a $C_3$–$C_8$ olefin.

18 Claims, No Drawings

PURIFICATION PROCESS FOR A HYDROFLUOROALKANE

The present invention relates to an improved purification process for a hydrofluoroalkane.

Whatever its method of preparation, a hydrofluoroalkane collected at the output of the synthesis reactor is generally contaminated with impurities comprising in particular unconverted reactants and/or various subproducts generated during the reaction or introduced with the reactants. The hydrofluoroalkane must therefore be subjected to a purification in order to separate therefrom, on the one hand, components which are more volatile than the hydrofluoroalkane, conventionally called light impurities, and, on the other hand, components which are less volatile than the hydrofluoroalkane, conventionally called heavy impurities.

A well known conventional purification process for hydrofluoroalkane consists of a separation by distillation in several steps. At the top of a first column, usually called the light-component column, the components which are more volatile than the hydrofluoroalkane are removed from the reaction mixture, the hydrofluoroalkane leaving this column at the bottom, in a mixture with the heavy impurities. The purification of the hydrofluoroalkane with respect to the heavy impurities is then conducted in a second distillation column, called the heavy-component column, supplied with the flux removed at the bottom of the light-component column, in which the purified hydrofluoroalkane constitutes the top fraction, and the heavy impurities constitute the bottom fraction.

This conventional process of purification by distillation has however proved unsatisfactory for obtaining a hydrofluoroalkane satisfying the purity specifications currently required. Hydrofluoroalkanes purified by this conventional process are in fact usually contaminated by a few ppm of proton acids and organic impurities, principally unsaturated halogenated organic impurities, which are particularly problematic in the final product because of their possible toxicity. The removal of such impurities then generally requires a subsequent finishing treatment.

The invention aims to remedy the shortcomings of the conventional process defined hereinabove by providing an improved process for purifying a hydrofluoroalkane by distillation, which makes it possible directly to obtain a hydrofluoroalkane which is almost free from halogenated organic purities and proton acids.

It has now been observed that, in the conventional process defined above, during the step of purifying the hydrofluoroalkane with respect to heavy impurities by distillation, a fraction of the hydrofluoroalkane and/or a fraction of some heavy impurities, principally halogenated organic compounds, may undergo degradation leading to the appearance of unsaturated halogenated organic compounds and proton acids. A possible cause of this degradation is the presence of traces of Lewis acids in the mixture to be separated. It has furthermore been observed that, even at room temperature, the presence of only 1 ppm of $FeCl_3$ in 1,1-dichloro-1-fluoroethane is sufficient to induce the dehydrochlorination of a significant fraction of this product to give 1-chloro-1-fluoroethene and hydrogen chloride. Another possible cause of this degradation is linked with the use of metal distillation columns, some metals being capable of inducing a certain degradation of halogenated compounds. Because their boiling point is lower than that of their precursors, these degradation compounds contaminate the hydrofluoroalkane removed at the top of the heavy-component column in the conventional process of purification by distillation.

Another object of the invention is then to provide a process for purifying a hydrofluoroalkane with respect to heavy impurities by distillation, in which the degradation of the hydrofluoroalkane and/or of the heavy impurities in the distillation column is greatly reduced.

The present invention relates then to a purification process for a hydrofluoroalkane, according to which the hydrofluoroalkane is subjected to a distillation in order to separate therefrom the impurities which are less volatile than the said hydrofluoroalkane, characterized in that the distillation is performed in the presence of an acid-scavenger.

It is observed that, when the distillation is performed according to the invention, in the presence of an acid-scavenger, neither the hydrofluoroalkane nor the organic impurities which accompany it (in particular halogenated organic impurities) are perceptibly degraded during the distillation, even when it is done in the presence of small quantities of Lewis acids.

The term hydrofluoroalkanes is generally intended to designate saturated hydrocarbons of the acyclic or alicyclic type, comprising at least one hydrogen atom and at least one fluorine atom. They may possibly also comprise at least one chlorine atom. Hydrofluoroalkanes as defined hereinabove generally comprise 1 to 6 carbon atoms. They generally conform to the formula $C_aH_bF_cCl_d$, in which a is an integer from 1 to 6, b is an integer from 1 to 13, c is an integer from 1 to 13 and d is an integer from 0 to 8, with $b+c+d=2a+2$ when the compound is acyclic, and with $b+c+d=2a$ when the compound is alicyclic. The process according to the invention is applicable in particular to acyclic compounds comprising from 1 to 4 carbon atoms, comprising at least one hydrogen atom and at least one fluorine atom. These compounds may furthermore contain at least one chlorine atom. They conform to the above formula in which a is an integer from 1 to 4, b is an integer from 1 to 9, c is an integer from 1 to 9 and d is an integer from 0 to 5. The process is most especially applicable to acyclic compounds having the above general formula, in which a is an integer equal to 2 or 3, b is an integer from 1 to 6, c is an integer from 1 to 6 and d is an integer from 1 to 4. As examples of hydrofluoroalkanes which can be treated by the process of the invention, mention may be made of the compounds with structural formula $CH_3CCl_2F$, $CH_3CClF_2$, $CH_3CHF_2$, $CH_3CF_3$, $CH_2FCH_2F$, $CH_2FCHF_2$, $CH_2FCF_3$, $CHF_2CCl_3$, $CHF_2CF_3$, $CHCl_2CF_3$, $CHClFCF_3$, $CHF_2CHF_2$, $CF_3CF_2CHF_2$, $CF_3CF_2CHCl_2$, $CF_2ClCF_2CHClF$, $CF_3CF_2CH_3$, $CF_3CH_2CF_2CH_3$ and $CF_3CH_2CH_2CF_3$. Good results have been obtained with the process according to the invention when it is applied to the purification of 1,1-dichloro-1-fluoroethane.

Hydrofluoroalkanes such as defined hereinabove, to which the process according to the invention is applicable, are generally obtained by reaction of d halogen, a proton acid or hydrogen with a saturated or unsaturated hydrocarbon which is possibly halogenated. By way of examples of such reactions, mention may be made of the synthesis of 1,1-dichloro-1-fluoroethane by hydrofluorination of vinylidene chloride or of 1,1,1-trichloroethane. Mention may also be made of the synthesis of 1,1,1,2-tetrafluoroethane by catalytic hydrofluorination of a compound of structural formula $CX_3CH_2Cl$, with X being Cl or F. The operational conditions under which these reaction are implemented are well known in the prior art. Whatever the hydrofluoroalkane synthesised and the method of preparation used, the hydrofluoroalkane leaving the synthesis reactor is generally contaminated by various impurities. These impurities may have varied origins and their nature depends on the hydrofluoroalkane synthesised and on the method of preparation used. They may involve in particular reactants which are not converted during the synthesis of the hydrofluoroalkane, impurities or derivatives of impurities present in the reactants, sub-products formed during the synthesis or alternatively reactants used or products obtained in a treatment subsequent to the synthesis for chemically converting some impurities accompanying the hydrofluoroalkane.

In the process according to the invention, the impurities which are less volatile than the hydrofluoroalkane are chemical compounds, generally organic chemical compounds, whose boiling point is higher than the boiling point of the hydrofluoroalkane subjected to the purification. As a general rule, it is desirable, for economic reasons, for the relative volatility, that is to say the ratio between the volatility of the hydrofluoroalkane and the volatility of the impurities which are less volatile than the hydrofluoroalkane, to be at least 1.05, and preferably at least 1.1.

In the rest of the text, the impurities which are less volatile than the hydrofluoroalkane, as described hereinabove, will be referred to as heavy impurities. The heavy impurities are normally $C_2$-$C_8$ halogenated organic compounds, principally saturated aliphatic hydrocarbons, and in particular hydrofluoroalkanes other than the one subjected to the purification.

In order effectively to inhibit the degradation of the hydrofluoroalkane to be purified and of the heavy impurities during the distillation, the acid-scavenger used in the process according to the invention must be highly reactive with respect to proton acids and halogens and have a vapor pressure which is sufficient for it to be distributed efficiently in the column where the distillation is performed. Acid-scavengers which can be used in the process according to the invention are in particular epoxides, amines and unsaturated hydrocarbons. As epoxides, mention may be made in particular of 1,2-epoxypropane, 1.2-epoxybutane, 1,2-epoxypentane, 1,2-epoxycyclohexane, 1,2-epoxyethylbenzene, epichlorohydrin and glycidol. As amines, mention may be made of diethylamine, dipropylamine, diisopropylamine, dibutylamine, diisobutylamine, triethylamine and tripropylamine. As unsaturated hydrocarbons, mention may be made in particular of propenes, butenes, methylbutenes, dimethylbutenes, pentenes, methylpentenes, dimethylpentenes, trimethylpentenes, hexanes, cyclopentene, cyclohexene and methylcyclopentene. According to the invention, the preferred acid-scavengers are $C_3$-$C_8$ unsaturated hydrocarbons. Among these unsaturated hydrocarbons, 2-methylbut-2-ene, 2-methylbut-1-ene, 3-methylbut-1-ene, 2- ethylbut-1-ene, pent-1-ene, pent-2-ene, 2-methylpent-1lene, 2-methylpent-2-ene, 3-methylpent-1-ene, 3-methylpent-2-ene, 4-methylpent-1-ene, 2,4,4-trimethylpent1-ene, hex-1-ene, hex-2-ene and hex-3-ene are particularly preferred.

In the case in which the process is applied to the purification of 1,1-dichloro-1-fluoroethane, the unsaturated hydrocarbon most particularly preferred as the acid-scavenger is 2-methylbut-2-ene. In this case, very good results have been obtained with industrial 2-methylbut-2-ene, usually called amylene, which furthermore contains a little 2-methylbut-1-ene.

All other things being equal, moreover, the optimum quantity of acid-scavenger to be used will depend on the nature of the hydrofluoroalkane to be purified, on the nature of the heavy impurities and on their concentration with respect to the hydrofluoroalkane to be purified, as well as on the acid-scavenger selected. It must then be determined in each particular case by routine laboratory work. In practice, it is recommended to use a quantity by weight of acid-scavenger at least equal to approximately 0.005 g per kilo of hydrofluoroalkane subjected to the distillation, and preferably greater than or equal to approximately 0.01 g. It is not generally advantageous for this quantity to exceed approximately 1 g per kilo of hydrofluoroalkane subjected to the distillation, and preferably approximately 0.1 g. Quantities between approximately 0.025 g and approximately 0.075 g per kilo of hydrofluoroalkane subjected to the distillation are recommended.

In the process according to the invention, the distillation is generally performed in one or more distillation columns, which are well known in the field of the art. In this embodiment of the process according to the invention, the best results are obtained when the acid-scavenger is distributed homogeneously throughout the distillation column. The acid-scavenger may be introduced at different levels in the column. In order to ensure maximum efficiency, it is sometimes desirable to introduce the acid-scavenger at several points of the column. The acid-scavenger may be introduced periodically into the column or, preferably, continuously.

In a first variant of the aforementioned embodiment of the process, the acid-scavenger is introduced at the top of the distillation column, for example by injecting it into a fraction of the condensed hydrofluoroalkane which is returned into the column as a reflux.

In a second variant of this embodiment of the process, the acid-scavenger is introduced at the bottom of the distillation column, for example by injecting it into a boiling vessel of the column.

In a third variant of this embodiment of the process, the acid-scavenger is added to the hydrofluoroalkane upstream of the distillation column.

In the aforementioned first variant of the process, it is possible to use an acid-scavenger having a boiling point markedly higher than that of the hydrofluoroalkane to be purified, for example a compound whose boiling point is greater by approximately 15° C. to approximately 50° C. with respect to the boiling point of the hydrofluoroalkane to be purified. This variant of the process is preferred when the level of content of acid-scavenger in the hydrofluoroalkane collected from the purification is to remain very low, for example less than 5 ppm.

When it is sought to obtain a residual level of content of acid-scavenger in the hydrofluoroalkane, collected from the purification, which is greater than 5 ppm, for example of the order of 10 to 100 ppm, according to the invention, an acid-scavenger is chosen whose boiling point is close to that of the hydrofluoroalkane, for example, a compound whose boiling point differs from that of the hydrofluoroalkane to be purified by no more than 15° C., preferably, a compound whose boiling point differs from that of the hydrofluoroalkane to be purified by no more than 10° C.

In a particularly preferred manner, an acid-scavenger would rather be used whose boiling point is 1 to 5° C. greater than that of the hydrofluoroalkane to be purified. Such an acid-scavenger may be used in all three variants of the process described hereinabove. The third variant of the process appears particularly advantageous, and is therefore preferred.

In the process according to the invention, it is necessary for the hydrofluoroalkane subjected to the distillation to be substantially free from impurities which are more volatile than it.

Impurities which are more volatile than the hydrofluoroalkane are inorganic or organic chemical compounds whose boiling point is less than the boiling point of the hydrofluoroalkane subjected to the purification.

In the rest of the text, impurities which are less volatile than the hydrofluoroalkane, as defined hereinabove, are referred to as light impurities. Typically, light impurities in the hydrofluoroalkane comprise inert gases such as nitrogen, proton acids such as hydrogen fluoride and hydrogen chloride, halogens such as chlorine and fluorine, hydrogen as well as certain organic compounds, principally $C_1$–$C_4$ organic compounds, most often halogenated, and possibly unsaturated.

The light impurities are removed from the hydrofluoroalkane by any appropriate technique, before introduction of the acid-scavenger into the mixture.

In one preferred embodiment of the process according to the invention, before the distillation, the hydrofluoroalkane is subjected to a predistillation in order to separate light impurities therefrom. The predistillation is a distillation which precedes the one intended to separate the heavy impurities from the hydrofluoroalkane, and which is carried out under controlled conditions in order to separate the light impurities from the hydrofluoroalkane. The predistillation is performed in one or more distillation columns.

It is generally desirable to add the acid-scavenger as rapidly as possible after the separation of the light impurities from the hydrofluoroalkane. For this purpose, in the preferred embodiment described hereinabove in which the light impurities are removed by a predistillation, the acid-scavenger may be injected into the boiling vessel of the column in which the predistillation is performed, at which place the hydrofluoroalkane is no longer contaminated with significant quantities of light impurities, in particular halogens or proton acids.

As described hereinabove, according to the embodiment variants of the process and the nature of the acid-scavenger used, the process according to the invention makes it possible to obtain the purified hydrofluoroalkane either almost free from the acid-scavenger, or containing small quantities by weight of acid-scavenger, for example of the order of 10 to 100 ppm. At this level of concentration, the acid-scavenger then performs the function of stabilizing the hydrofluoroalkane, both for storage and for subsequent uses, in particular as a solvent.

The invention has numerous advantages. It makes it possible in particular to perform the distillation in a column made of ordinary steel. It also makes it possible to perform the distillation in the presence of Lewis acids, which are regularly present in hydrofluoroalkanes to be purified because of their frequent use as catalysts, during the synthesis of the hydrofluoroalkanes. The inhibition of the formation, within the distillation column, of unsaturated organic products and proton acids which are lighter than the hydrofluoroalkanes subjected to the purification, makes it possible to recover the latter at the top of the column, which operation is easier than withdrawal from an intermediate tray. The absence of compounds which are more volatile than the hydrofluoroalkane in the column furthermore removes the necessity for purging the top of the column, which improves the overall yield of the process. The invention furthermore makes it possible to conduct the distillation at higher pressures and temperatures than in the absence of the acid-scavenger, without any degradation of the hydrofluoroalkane or of the heavy impurities being observed. It also makes it possible to obtain a hydrofluoroalkane satisfying the strictest of purity specifications without needing to implement a finishing treatment for the product.

The examples whose description follows serve to illustrate the invention. Example 1, produced according to a conventional process of purification by distillation, is given by way of reference. Examples 2 and 3 are in accordance with the invention.

EXAMPLE 1 (FOR REFERENCE)

1,1-Dichloro-1-fluoroethane obtained by hydrofluorination of vinylidene chloride then having undergone a treatment of chlorination of the unsaturated impurities, in the presence of $FeCl_3$, is subjected to a predistillation in order to purify it with respect to the light impurities. For this purpose, it is introduced into a first stripping column (light-component column) under a pressure of 2.1 bar. The excess chlorine used in the preceding chlorination step is removed at the top of the column, and the mixture of 1,1-dichloro-1-fluoroethane and the heavy impurities comprising in particular chlorinated saturated compounds produced in the step of chlorination of the unsaturated impurities, leaves the light-component column at the bottom. This mixture is then introduced into a second distillation column (heavy-component column), operating at a pressure of 1.5 bar. In this column, the mixture undergoes a distillation in order to separate the 1,1-dichloro-1-fluoroethane from the impurities which accompany it. The 1,1-dichloro-1 -fluoroethane is there withdrawn at the top of the column and the heavy impurities are removed at the bottom. The reflux ratio is equal to 2.

The mean concentration of 1-chloro-1-fluoroethene in the 1,1-dichloro-1-fluoroethane withdrawn at the top is 5 mg per kilo of 1,1-dichloro-1-fluoroethane.

EXAMPLE 2 (ACCORDING TO THE INVENTION)

Every point of the above Example 1 is repeated, but 30 mg of amylene per kilo of mixture is injected into the boiling vessel of the light-component column. The mean concentration of 1-chloro-1-fluoroethene in the 1,1-dichloro-1-fluoroethane withdrawn at the top is less than 0.2 mg per kilo of 1,1-dichloro-1-fluoroethane.

The purified 1, 1-dichloro-1-fluoroethane contains on average 20 mg of amylene per kilo.

EXAMPLE 3 (ACCORDING TO THE INVENTION)

Every point of the above Example 1 is repeated, but 30 mg of amylene per kilo of 1,1-dichloro-1-fluoroethane returned to the heavy-component column as reflux is injected.

The mean concentration of 1-chloro-1-fluoroethene in the 1,1-dichloro-1-fluoroethane withdrawn at the top is less than 0.2 mg per kilo of 1,1-dichloro-1-fluoroethane and the purified 1,1-dichloro-1-fluoroethane contains on average 50 mg of amylene per kilo.

I claim:

1. A purification process for a hydrofluoroalkane, comprising:

distilling said hydrofluoroalkane to separate therefrom impurities which are less volatile than said hydrofluoroalkane, said distillation performed in the presence of approximately 0.005 g to approximately 1 g of an acid-scavenger per kilo of hydrofluoroalkane subjected to the distillation, and separating said impurities from said hydrofluoroalkane.

2. The process according to claim 1, wherein a hydrofluoroalkane is used which has undergone a predistillation in order to separate therefrom impurities which are more volatile than the said hydrofluoroalkane.

3. The process according to claim 1, wherein the acid-scavenger is a $C_3$–$C_8$ unsaturated hydrocarbon.

4. The process according to claim 1, wherein the quantity of acid-scavenger is approximately 0.01 g to 0.1 g per kilo of hydrofluoroalkane subjected to the distillation.

5. The process according to claim 1, wherein the acid-scavenger has a boiling point higher by approximately 15° C. to approximately 50° C. than the boiling point of the hydrofluoroalkane to be purified, and said acid-scavenger is introduced at the top of the column in which the distillation is performed.

6. The process according to claim 1, wherein an acid-scavenger is used whose boiling point differs from that of the hydrofluoroalkane to be purified by no more than 15° C.

7. The process according to claim 6, wherein an acid-scavenger is used whose boiling point is from 1° to 5° C. higher than that of the hydrofluoroalkane to be purified.

8. The process according to claim 6, wherein the acid-scavenger is added to the hydrofluoroalkane upstream of the column in which the distillation is performed.

9. The process according to claim 1, wherein said hydrofluorocarbon is 1,1-dichloro-1-fluoroethane.

10. The process according to claim 9, wherein 2-methylbut-2-ene is the acid-scavenger.

11. The process according to claim 6 wherein said hydrofluoroalkane after said impurities are separated contains from 10 to 100 mg of acid-scavenger per kilo.

12. The process according to claim 7 wherein said hydrofluoroalkane after said impurities are separated contains from 10 to 100 mg of acid-scavenger per kilo.

13. The process according to claim 8 wherein said hydrofluoroalkane after said impurities are separated contains from 10 to 100 mg of acid-scavenger per kilo.

14. The process according to claim 9 wherein said hydrofluoroalkane after said impurities are separated contains from 10 to 100 mg of acid-scavenger per kilo.

15. The process according to claim 10 wherein said hydrofluoroalkane after said impurities are separated contains from 10 to 100 mg of acid-scavenger per kilo.

16. A purification process for 1,1-dichloro-1-1-fluoroethane, comprising distilling said 1,1-dichloro-1-fluorethane to separate therefrom impurities which are less volatile than said 1,1-dichloro-1-fluoroethane, said distillation performed in the presence of an acid-scavenger.

17. The process according to claim 16, wherein the scavenger is a $C_3$–$C_8$ unsaturated hydrocarbon.

18. The process according to claim 16, wherein the acid-scavenger is 2-methylbut-2-ene.

* * * * *